US009020157B2

(12) United States Patent
Penketh et al.

(10) Patent No.: US 9,020,157 B2
(45) Date of Patent: Apr. 28, 2015

(54) ACTIVE NOISE CANCELLATION SYSTEM

(71) Applicant: Wolfson Microelectronics plc, Edinburgh (GB)

(72) Inventors: Julian Penketh, Oldham (GB); Abid Rashid, Reading (GB)

(73) Assignee: Cirrus Logic International (UK) Limited, Edinburgh (GB)

( * ) Notice: Subject to any disclaimer, the term of this patent is extended or adjusted under 35 U.S.C. 154(b) by 315 days.

(21) Appl. No.: 13/796,120

(22) Filed: Mar. 12, 2013

(65) Prior Publication Data

US 2013/0243214 A1 Sep. 19, 2013

Related U.S. Application Data

(60) Provisional application No. 61/611,868, filed on Mar. 16, 2012.

(51) Int. Cl.

| | |
|---|---|
| ***A61F 11/06*** | (2006.01) |
| ***G10K 11/16*** | (2006.01) |
| ***H03B 29/00*** | (2006.01) |
| ***G10K 11/175*** | (2006.01) |
| ***G10K 11/178*** | (2006.01) |

(52) U.S. Cl.

CPC .......... *G10K 11/175* (2013.01); *G10K 11/1784* (2013.01); *G10K 2210/1081* (2013.01); *G10K 2210/3028* (2013.01); *G10K 2210/3056* (2013.01); *G10K 2210/503* (2013.01)

(58) Field of Classification Search

None

See application file for complete search history.

(56) References Cited

U.S. PATENT DOCUMENTS

2010/0278352 A1 11/2010 Petit et al.
2012/0148067 A1 * 6/2012 Petersen et al. ................. 381/92

FOREIGN PATENT DOCUMENTS

GB 2 455 300 A 6/2009
JP 3186892 B2 7/2001
JP 2001-352594 A 12/2001

* cited by examiner

*Primary Examiner* — Regina N Holder

(74) *Attorney, Agent, or Firm* — Dickstein Shapiro LLP

(57) ABSTRACT

A noise cancellation system generates a noise cancellation signal from a signal representing ambient noise by signal processing. The signal processing applies a controllable gain value, and includes a high pass filter with a controllable cut-off frequency. A control block detects a wind amplitude. The cut-off frequency of the high pass filter is controlled based on the detected wind amplitude. A low pass function is applied to the detected wind amplitude, and the controllable gain is adjusted based on the output of the low pass function.

26 Claims, 6 Drawing Sheets

ACTIVE NOISE CANCELLATION SYSTEM

This application claims the benefit of U.S. Provisional Application No. 61/611,868, filed on Mar. 16, 2012.

BACKGROUND OF THE INVENTION

1. Field of the Invention

This invention relates to an active noise cancellation system, and to a method of active noise cancellation.

2. Description of the Related Art

It is known to provide a feedforward active noise cancellation system, in which one or more microphones are used to generate an electrical signal representative of the ambient noise. This ambient noise signal is passed to a filter, to generate a noise cancellation signal. The noise cancellation signal is applied to a speaker, which is located close to the user's ear, for example in an earphone device or in a handset that is intended to be held close to the ear. By suitable choice of the filter, the effect of the noise cancellation signal is to generate sounds that are equal in magnitude, but opposite in phase, to the ambient noise arriving at the user's ear, so that the sound waves cancel, and the noise that reaches the user's ear is reduced.

One typical use of such an active noise cancellation system is in a sound reproduction device, where the noise cancellation signal is added to a wanted sound signal, for example representing music or speech, before being applied to the speaker.

It is also known to provide an element of feedback, by locating an error microphone close to the entrance to the user's ear canal, and using the signal detected by the error microphone to adapt the filter that is used to generate the noise cancellation signal. In a fully adaptive system, the error signal is used to adapt the frequency response of the filter. In a simpler system, the error signal is used to adapt the gain of the filter, without altering the frequency response.

It is commonly required to use active noise cancellation in systems that are intended to be used outside, where there might be wind. For example, mobile telephone handsets and playback devices are often used in such conditions. However, the effect of conventional active noise cancellation systems in the presence of wind noise is to magnify the wind noise, rather than cancel it. This problem arises because wind is a randomly varying air pressure that is felt more than heard, whereas ambient noise is audible. The ambient noise can be cancelled by an inverted version of the signal generated by the noise microphone. However, although wind is not heard to a great extent, it causes turbulence around the noise microphone, and thus generates a component of the noise signal. A corresponding component of the noise cancellation signal will be generated, and will cause the speaker to produce sounds. However, the inverted version of the wind noise component has no audible counterpart to cancel, and so the wind noise is made more audible by the active noise cancellation system. Even a small gust of wind, that would not itself be very loud or disturbing directly at the ear, can yield an annoying level of wind noise.

SUMMARY OF THE INVENTION

According to an aspect of the present invention, there is provided a method of controlling a noise cancellation system, wherein the noise cancellation system comprises:

an input, for receiving a signal representing ambient noise; and a signal processing block, for generating a noise cancellation signal from the signal representing ambient noise, wherein the signal processing block includes a controllable gain value, and a high pass filter with a controllable cut-off frequency, the method comprising:

detecting an amplitude of wind;

controlling the cut-off frequency of the high pass filter based on the detected wind amplitude; and applying a low pass function to the detected wind amplitude, and controlling the controllable gain value based on the output of the low pass function.

According to a second aspect of the present invention, there is provided a noise cancellation system, comprising:

an input, for receiving a signal representing ambient noise;

a signal processing block, for generating a noise cancellation signal from the signal representing ambient noise, wherein the signal processing block includes a controllable gain value, and a high pass filter with a controllable cut-off frequency; and a control block, wherein the control block is adapted to:

detect an amplitude of wind;

control the cut-off frequency of the high pass filter based on the detected wind amplitude; and apply a low pass function to the detected wind amplitude, and control the controllable gain value based on the output of the low pass function.

According to a third aspect of the present invention, there is provided a listening device, comprising a noise cancellation system according to the second aspect.

This has the advantage that the noise cancellation system does not generate a signal that would have the effect of magnifying the wind noise heard by the user.

BRIEF DESCRIPTION OF THE DRAWINGS

For a better understanding of the present invention, and to show how it may be put into effect, reference will now be made, by way of example, to the accompanying drawings, in which.

DETAILED DESCRIPTION OF THE PREFERRED EMBODIMENTS

Figure 1:
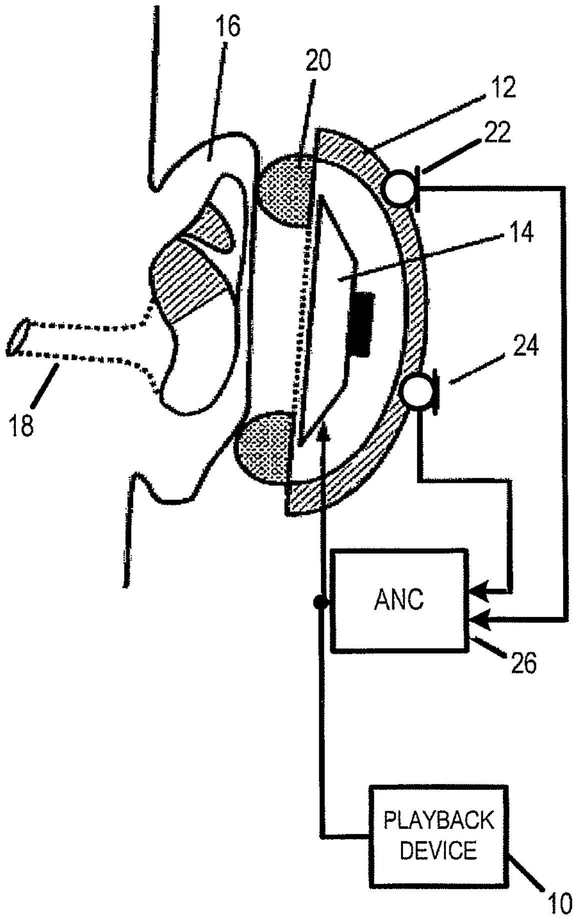
FIG. 1 is a schematic illustration of a sound reproduction system in accordance with an aspect of the invention.

FIG. 1 shows a sound reproduction system in accordance with an aspect of the present invention. Specifically, FIG. 1 shows a sound reproduction system having a playback device 10, which might for example be a personal computer, portable music player, games console, communications handset or the like. The sound reproduction system also includes at least one earphone 12. Typically, the system will include a pair of earphones, but the invention can be described with reference to just one earphone.

Electrical signals representing wanted sounds such as speech or music are supplied from the playback device 10 to a speaker 14 mounted in the earphone 10, in order to generate the wanted sounds. The earphone 12 is intended to be located adjacent to the ear 16 of a user, in order to direct the generated sounds into the ear canal 18 of the user. In this case, the earphone 12 is of the type with a cushion 20 to allow the earphone 12 to be worn comfortably on the ear 16 of the user.

Two microphones 22, 24 are located on the outside of the earphone 12, positioned such that they can detect pressure variations resulting either from ambient noise or from wind in the vicinity of the user. Electrical signals generated by the microphones 22, 24 are supplied to an active noise cancellation (ANC) circuit 26, which generates a noise cancellation signal, as described in more detail below. Specifically, in the embodiment of the invention described in more detail below, the signal generated by a first microphone 22 are used to represent the ambient noise in the vicinity of the user, while the signals generated by the first microphone 22 and second microphone 24 are used to detect wind in the vicinity of the earphone, and as such are used in the control of the ANC circuit 26. In other embodiments of the invention, multiple microphones can be used to detect the ambient noise in the vicinity of the user.

The noise cancellation signal is supplied to the speaker 14, which causes corresponding sounds to be generated and directed into the ear canal 18 of the user. The intention of the ANC circuit 26 is to generate a noise cancellation signal that will produce a sound that will cancel the ambient noise when it reaches the user's ear. As is known, this requires the ambient noise signal to be processed in a way that takes account of the frequency response of the microphone 22 and the speaker 14, and that takes account of the frequency response characteristic of the path taken by the ambient noise as it approaches the user's ear around the earphone 12. The ANC circuit 26 must also invert the signal, so that the corresponding speaker output cancels the ambient noise that would otherwise be heard by the user.

The ANC circuit 26 can be provided within the playback device 10, for example as a dedicated integrated circuit. Alternatively, the functionality of the ANC circuit 26 as described herein can be provided as a software function running on a digital signal processor within the playback device. As a further alternative, the ANC circuit can be associated with an earphone or a pair of earphones, for example in a pod carried on a cable that connects the earphone or earphones to the playback device 10.

Figure 2:
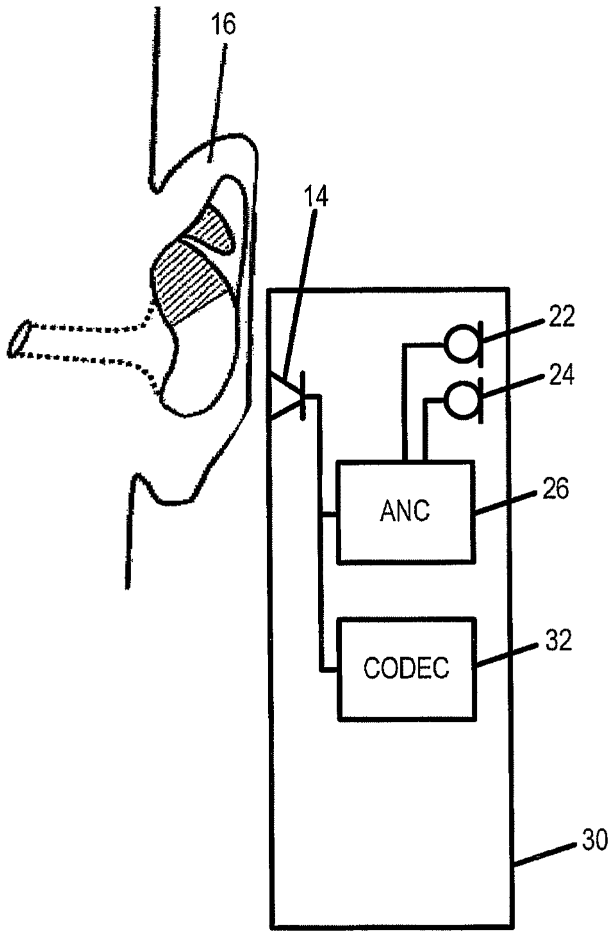
FIG. 2 is a schematic illustration of a second sound reproduction system in accordance with an aspect of the invention.

FIG. 2 shows a further alternative sound reproduction system, in the form of a mobile handset 30. In this embodiment, the mobile handset comprises an audio codec 32, for receiving signals from internal storage of the handset 30 or from wireless transceiver circuitry of the handset 30, and for generating signals to be applied to a speaker 14 for generating wanted sounds representing stored music or speech, or the remote side of a mobile phone conversation, for example. Further description of the operation of the codec 32, and of the other features of the handset 30, is not required for an understanding of the present invention.

As is conventional, the speaker 14 is mounted in the handset 30 at a location that is intended to be held close to the ear 16 of the user. The handset 30 also includes microphones 22, 24, for example located at opposite sides on the rear face of the handset 30, for detecting pressure variations resulting either from ambient noise or from wind in the vicinity of the user. Signals from the microphones 22, 24 are supplied to an active noise cancellation (ANC) circuit 26, which generates a noise cancellation signal, in the same manner as the ANC circuit 26 of FIG. 1, and as described in more detail below.

In FIG. 2, the ANC circuit 26 can be provided as a dedicated integrated circuit within the handset 30, or as a dedicated part of the codec 32, or as a function running on a digital signal processor within the codec 32.

Figure 3:
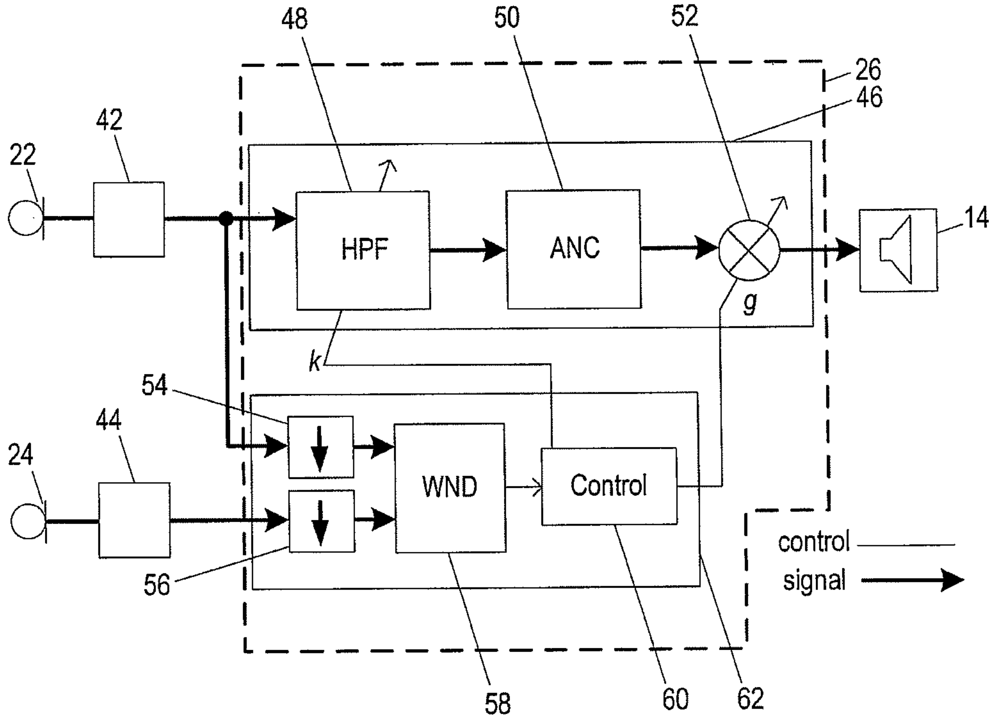
FIG. 3 is a schematic illustration of a noise reduction system in the sound reproduction system of FIG. 1.

FIG. 3 shows in more detail one exemplary embodiment of the active noise cancellation (ANC) circuit 26, for example for use in the sound reproduction system of FIG. 1 or 2.

In this embodiment, the ANC circuit 26 operates entirely on digital signals, although it is also possible to perform the required signal processing in the analog domain. Thus, in this embodiment, the signals from the microphones 22, 24 are passed to respective analog-digital converters 42, 44 before being passed to the ANC circuit 26.

The digital signal from the first microphone 22 and first analog-digital converter 42, representing the ambient noise, is passed to a hardware signal processing block 46, comprising a high pass filter 48, having a cutoff frequency that is controlled by an input parameter k. The filtered signal is passed to an ANC signal processor 50. The ANC signal processor 50 performs a filtering operation, in which the ambient noise signal is processed in a way that takes account of the frequency responses of the microphone 22 and the speaker 14, and that takes account of the frequency response characteristic of the path taken by the ambient noise as it approaches the user's ear around the earphone 12, and that inverts the signal, to generate a noise cancellation signal that can be applied to the speaker 14. The noise cancellation signal is also passed through a multiplier 52, where it is multiplied by a controllable gain value g, before being applied to the speaker 14.

In this embodiment of the invention, the signal processing is performed in such a manner as to enable sufficient time alignment to be achieved between the ambient noise and the sounds generated by the speaker 14, resulting from the application of the noise cancellation signals, as they reach the user's ear. This is achieved by using filters that introduce only small delays into the signals. For example, the analog-digital converters 42, 44 and the hardware signal processing block 46 can be such that they operate at high sample rates, for example in the region of 2.5 MHz, and have low latency.

In this illustrated embodiment, the parameter k, controlling the cutoff frequency of the high pass filter 48, and the gain value g, applied by the multiplier 52, are controlled so as to reduce as far as possible the audible effects of wind impinging on the microphones 22, 24.

In this embodiment, the parameter k, and the gain value g, are controlled at a slower rate than the sample rate of the digital signals. Thus, the signals from the analog-digital converters 42, 44 are passed to respective downsampling blocks 54, 56, for example in the form of CIC decimators, to reduce their sample rates. In this illustrated embodiment, the control circuitry operates at a sample rate of 8 kHz, and so the downsampling blocks 54, 56 reduce the sample rates by a factor of 320.

The signals generated by the downsampling blocks 54, 56 are passed to a wind noise detection block 58, which determines the amplitude of the signal resulting from the wind on the microphones 22, 24.

The amplitude detected by the wind noise detection block 58 is passed to a control block 60, which generates control signals for adapting the value of the parameter k, and the gain value g.

The functions of the wind noise detection block 58, and the control block 60, can be implemented in software 62, for example running on a digital signal processor.

The wind noise detection block 58 determines an amplitude for the wind. Many techniques are available for detecting a wind noise amplitude, and any of these techniques can be used in the system of the present invention. However, in the embodiment described herein, the wind noise detection block 58 uses the property of wind that it is highly non-stationary, i.e. that, from one sample to another, the signals are highly uncorrelated. More specifically, in the embodiment described herein, in which the ANC system uses signals from a pair of microphones, the spatial separation of the microphones creates the temporal separation needed for the calculation of a cross-correlation function (CCF) that is compared to an auto-correlation function (ACF).

Figure 4:
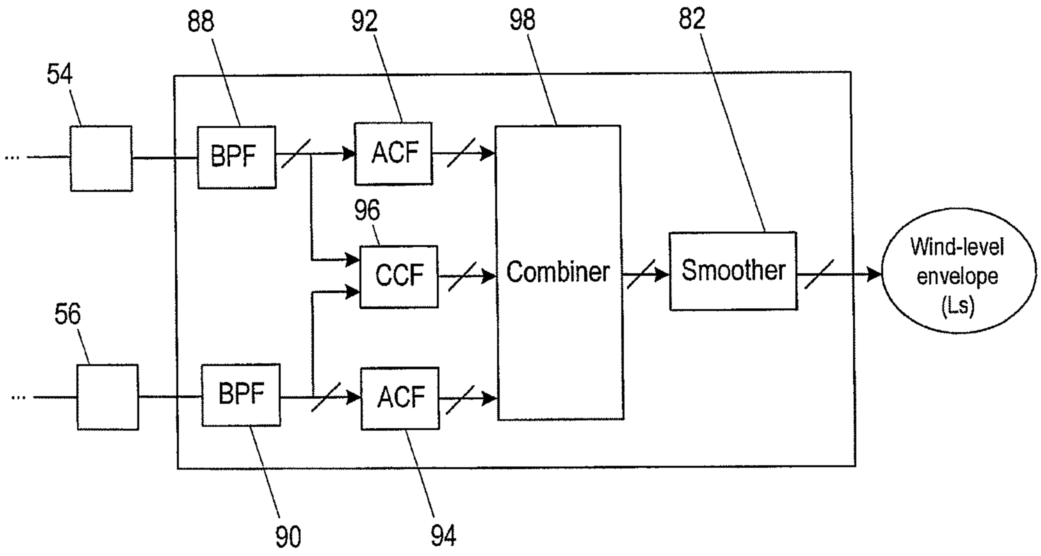
FIG. 4 illustrates the wind detection block in the system of FIG. 3.

FIG. 4 shows in schematic form the form of the wind noise detection function performed in software in the wind noise detection block 58. Signals are received from the noise microphones 22, 24, at sample rates of 8 kHz, after passing through the respective ADCs 42, 44 and respective downconverters 54, 56.

The determination of the wind level is based on a correlation between the signals received from the noise microphones 22, 24.

The received signals are passed to respective band-pass filters 88, 90, which can be seen as the combination of a high-pass filter with low cut-off (for example at 50 Hz), in order to remove any DC bias offset between the microphone outputs, and a 400 Hz low-pass filter to emphasize the frequency band where wind energy is most prevalent.

The filtered signals are passed to respective blocks 92, 94 for calculating the respective auto-correlations of the signals, and they are both passed to a block 96 for calculating the cross-correlation between them.

The sub-blocks 92, 94 for computing the auto-correlation function (ACF) and the sub-block 96 for computing the cross-correlation function (CCF) can operate with a block-based implementation, or on a sample-by-sample basis.

In either case, the aim is to calculate the correlation $R_{xy}(m)$ between two data streams x, y. In the case of the auto-correlation functions, the two data streams x, y both represent the stream of samples from the respective microphone, after the band pass filtering described above, and so they are both the same. In the case of the cross-correlation function, the two data streams x, y represent the streams of samples from the two microphones, after the band pass filtering described above.

Thus:

$$R_{xy}(m) = \frac{1}{N}\sum_{n=0}^{N-1} x(n)y(n+m)$$

where n is the sample value and m is a shift (or lag) operator. In this implementation, we are using a relatively low sample rate, and so it is sufficient to compute only the zero-lag, i.e. m=0, and the m=+1 and m=−1 lags in order to capture correlating data between the two microphones.

Detection of wind depends upon its highly non-stationary nature, where from one sample to another, the signals are highly uncorrelated. With a pair of microphones, the spatial separation creates the temporal separation needed for the calculation of a cross-correlation function (CCF) that we can compare to an auto-correlation function (ACF). The correlation properties of typical sound signals, such as speech, music, or ambient noise, will not vary so much during the time-lag between one microphone and the other. Thus, the cross-correlation function (CCF) result is similar to the auto-correlation function (ACF) result: $R_{xy} \approx R_{xx}$.

However, the presence of wind hitting the microphones, and creating random turbulence, will decorrelate the relationship between the signals from the two microphones. Thus, $R_{xy} \neq R_{xx}$, and therefore, as the wind level increases, the level of cross-correlation steadily decreases relative to the auto-correlation. A comparison between the cross-correlation function and the auto-correlation functions can therefore be used to obtain a value for the wind level.

The outputs of the sub-blocks 92, 94 for computing the auto-correlation function (ACF) and the sub-block 96 for computing the cross-correlation function (CCF) are therefore passed to a combiner 98 for calculating the instantaneous wind level. The correlation values can be used in different ways to determine the wind level.

For example, in this illustrated embodiment, only the central value (m=0) of each auto-correlation function (ACF) is calculated, representing the power of the respective signal, while the value used for the cross-correlation function (CCF) is the largest of the cross-correlation values obtained for the different values of m. In addition, since the cross-correlation function (CCF) can have a negative value if one input is inverted with respect to the other, it is the absolute value that is used.

As mentioned above, the wind-noise detection algorithm depends on the level of correlation between the signals from the two microphones 22, 24, where the cross-correlation function (CCF) is denoted $R_{12}$. In the absence of any gain mismatch, an acoustic wave impinging on the pair of microphones will result in $R_{12}$ being close to unity. However, if there is a significant constant level mismatch between the signals from the two microphones, then an acoustic wave impinging on them will have a reduced $R_{12}$.

In the case where the microphones 22, 24 are spaced very close together (for example where the propagation delay between them is less than one sample interval), then a simple combining function may be used to obtain a value, L, for the wind level, as the two auto-correlation functions $R_{11}$, $R_{22}$ will have very similar values.

Thus:

$$L = 1 - \frac{|R_{12}|}{R_{11}}$$

In this case, the system could just be tuned to provide the appropriate wind-level value, L, for a certain microphone bias (assuming that the bias remains approximately constant for all devices of one model).

An alternative formula for calculating wind level, using the ACFs of both microphones in the denominator, is:

$$L = 1 - \frac{\left[\frac{|R_{12}|}{R_{11}} + \frac{|R_{12}|}{R_{22}}\right]}{2} = 1 - \left[\frac{|R_{12}|}{2R_{11}} + \frac{|R_{12}|}{2R_{22}}\right],$$

which is equivalent to:

$$L = 1 - \left[\frac{2|R_{12}|R_{22} + 2|R_{12}|R_{11}}{4R_{11}R_{22}}\right].$$

However, this has the effect that, when the ACF of one microphone is very small compared to the other, the ratio could exceed unity, even when the CCF value is small enough to suggest that wind is present. This situation could be caused by a faulty microphone, but could equally be caused in normal use by the user's hand covering the microphone.

Thus, a further alternative is to calculate the wind level as:

$$L = 1 - \frac{|R_{12}|}{(R_{11} + R_{22})/2},$$

where:

$R_{11}$ is the auto-correlation of the signal from the first microphone 22 with no time lag, $R_{22}$ is the auto-correlation of the signal from the second microphone 24 with no time lag, and $R_{12}$ is the cross-correlation between the signals from the first microphone 22 and the second microphone 24 at the time lag m that produces the maximum cross-correlation.

This allows for an acceptable calculation of the wind level, even if there is a relatively large mismatch between the noise microphones.

A still further alternative is to compare the two ACFs and use only the larger of the two. Thus, the wind level is calculated as:

$$L = 1 - \frac{|R_{12}|}{\max(R_{11}, R_{22})}$$

This approach avoids problems that result from one microphone having a very low gain, or being completely shielded from the wind.

It will be appreciated that the wind level can be calculated in many other ways, and that the wind level value can be presented in many other ways that would be equivalent to this. However, in these examples, the fractional wind level value, L, can range from 0.0, representing no wind, to 1.0, representing maximum wind.

That is, if no wind is present, then the time-domain signals received by the two microphones 22, 24 should be correlated to a high degree and L will approach zero. On the other hand, as the strength of the wind increases then $R_{12}$ decreases, and so L approaches unity.

The combiner 98 thus determines the instantaneous level of wind during one block of input signal samples. In one illustrative example, with the wind detection block receiving signals from the microphones at a downsampled sampled rate of 8 kHz, a block size of 64 is used for calculating the ACF and the CCF values, so that wind level values are generated at a sample rate of 125 Hz. Since the wind level can fluctuate rapidly, the outputs of the combiner 98 are passed to a smoothing filter 82 to generate an output $L_s$ representing the wind envelope.

Figure 5:
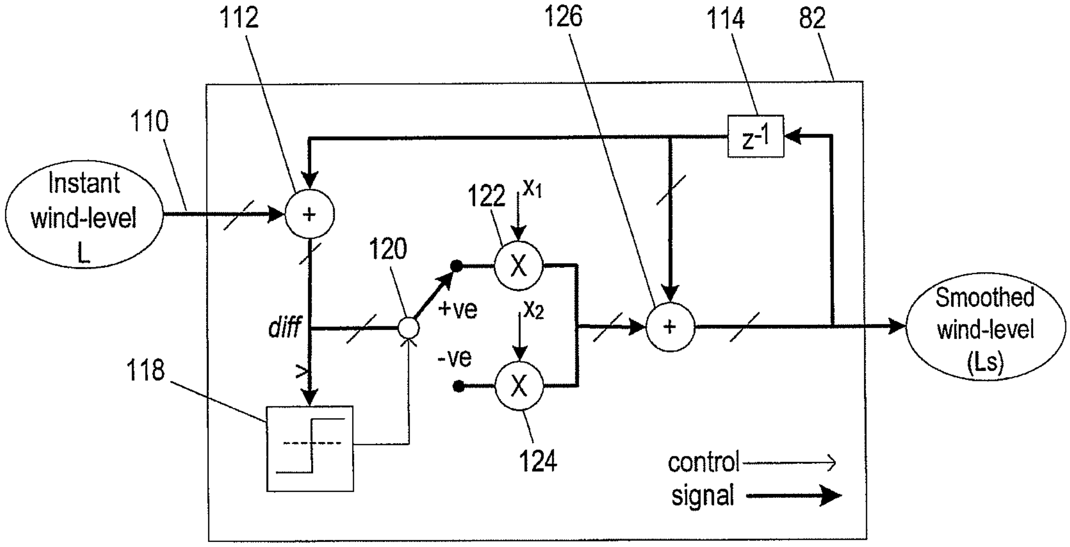
FIG. 5 illustrates the smoother in the wind detection block of FIG. 4.

FIG. 5 is a block diagram, illustrating the form of the smoothing filter function 82.

Values L, representing the instantaneous wind level during one block of samples, are applied to an input 110 of the smoother 82, and hence to a first input of an adder 112. As mentioned above, the smoother 82 generates a smoothed output value (Ls) in each period of one block of samples, and each output value (L) is applied to a delay element 114. The output of the delay element 114, which is therefore equal to the output value during the previous input period (that is, during the previous period corresponding to one block of signal samples, during which one wind level value is calculated), is applied to a second input of the adder 112, and is subtracted from the present input value (L).

The result of the subtraction represents the difference between the present input value and the previous output value. This difference value is passed to a slicer block 118, which determines whether the difference is positive or negative. If the difference is positive, i.e. the present input value is greater than the previous output value, a switch 120 is moved to a first position, so that the difference value is applied to a first input of a first multiplier 122. If the difference is negative, i.e. the present input value is smaller than the previous output value, the switch 120 is moved to a second position, so that the difference value is applied to a first input of a second multiplier 124.

The first multiplier 122 receives on its second input a coefficient $\alpha_1$ to be applied when the wind level is increasing, which in one embodiment in which the signal sample rate is 8 kHz, and wind level values are calculated at a rate of 125 Hz, might for example be 0.3333. The second multiplier 124 receives on its second input a coefficient $\alpha_2$ to be applied when the wind level is decreasing, which in the embodiment with a 125 Hz input sample rate might for example be 0.029. Having a larger attack coefficient $\alpha_1$ means that the system reacts quickly to a sudden onset of wind, while a smaller decay coefficient $\alpha_2$ allows smoothness of operation as the wind stops.

The output of the active one of the multipliers 122, 124 is passed to a second adder 126, where it is added to the previous output value of the smoother 82, as output by the delay element 114.

The output of the second adder 126 is the taken as the present output (Ls) of the smoother 82. The smoother produces output values at the same rate as it receives input values, and so the smoothed wind level values are generated at a sample rate of 125 Hz.

Thus, the smoother 82 brings the output value towards the input value over a number of sample periods, and the output of the smoother 82 is taken as the output of the wind noise detection block 58, and applied to the control block 60.

Figure 6:
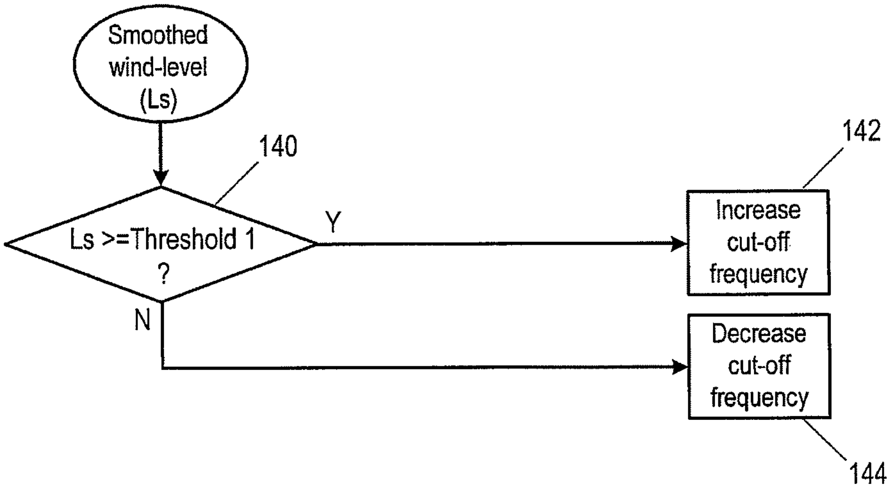
FIG. 6 is a flow chart, illustrating a first aspect of the operation of the control block 60.

FIG. 6 is a first flow chart, illustrating a first aspect of the operation of the control block 60.

In step 140, the smoothed value of the wind level, generated by the smoother 82 of the wind detection block 58, is compared with a first threshold value.

If the smoothed value is equal to exceeds the first threshold value, the process passes to step 142, in which the cut-off frequency of the high pass filter 48 is increased by means of the control parameter k, provided that this increase does not take the cut-off frequency above an upper limit. By contrast, if the smoothed value is lower than the first threshold value, the process passes to step 144, in which the cut-off frequency of the high pass filter 48 is decreased by means of the control parameter k, provided that this decrease does not reduce the cut-off frequency below a lower limit.

For example, the lower limit cut-off frequency might be in the region of 20 Hz, while the upper limit cut-off frequency might be in the region of 450 Hz, while the cut-off frequency might be changed in steps of, for example, approximately 50 Hz. As the smoother 82 generates output values at a rate of 125 Hz, this means that the cut-off frequency can be changed from the lower limit to the upper limit (or from the upper limit to the lower limit) in less than 0.1 seconds.

This mechanism allows the ANC circuit 26 to react quickly to changes in the wind level, for example in the case of sudden gusts of wind.

More specifically, adjusting the high pass filter cut-off frequency allows wind noise (which is strongest up to around 500 Hz) to be reduced by a gradual amount without affecting the output level across the rest of its operational range (which might for example be from around 200 Hz to around 1.2 kHz). If the gain of the ANC system is reduced across the whole ANC frequency band, rapidly varying wind produces an uncomfortable experience for the user. Therefore, it is advantageous to adjust the cut-off frequency of the high-pass filter, rather than adjust the gain, in response to rapid changes in wind level.

Figure 7:
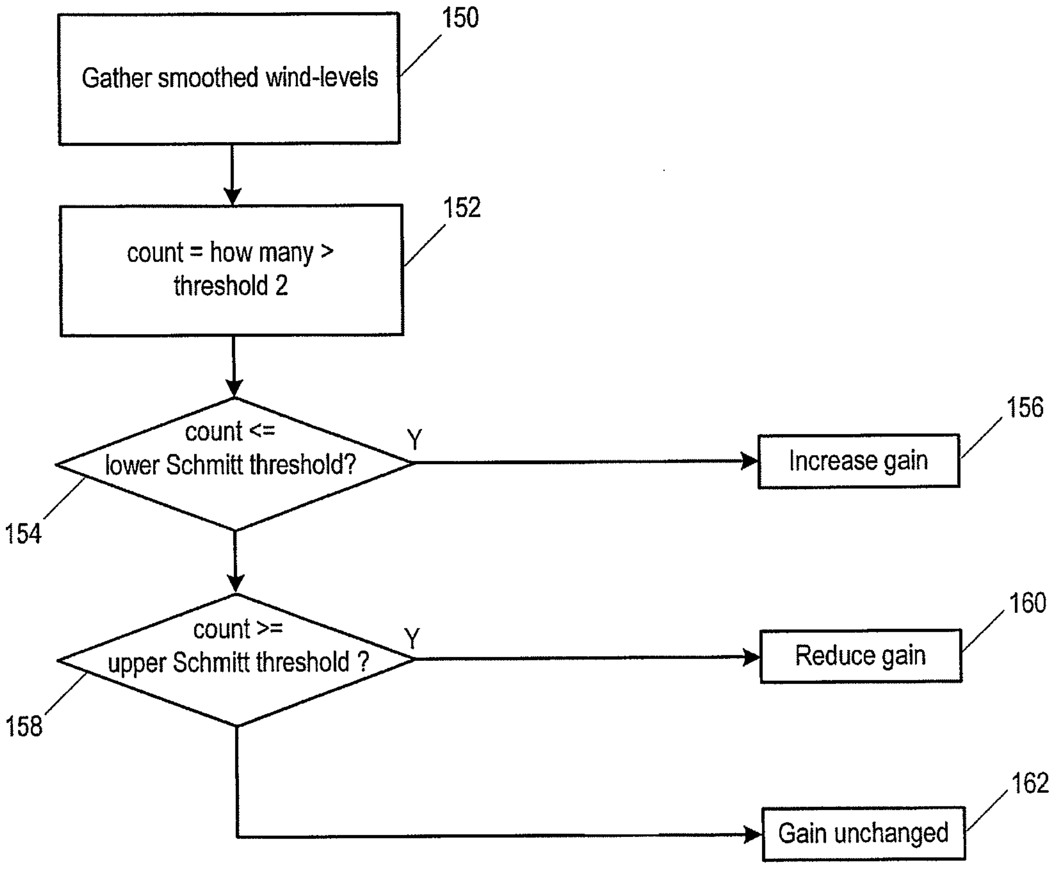
FIG. 7 is a first flow chart, illustrating a second aspect of the operation of the control block 60.

FIG. 7 is a second flow chart, illustrating a second aspect of the operation of the control block 60. In this aspect of the operation, the gain of the ANC system is controlled, using a Schmitt trigger mechanism, so that the gain does not react to quickly varying values of the wind level, but only to sustained changes.

In step 150, multiple smoothed values of the wind level, generated by the smoother 82 of the wind detection block 58, are gathered. For example, a number in the range of ten to fifty successive smoothed values might be gathered.

In step 152, it is counted how many of these values exceed a second threshold value, which is typically higher than the first threshold value used in the method of FIG. 6, and represents a relatively strong wind.

In step 154, it is determined whether the counted number is equal to or exceeds a lower Schmitt trigger threshold. In an illustrative example, the lower Schmitt trigger threshold might be three values out of ten. If so, the process passes to step 156, in which the gain value g, applied by the multiplier 52, is ramped up, provided that this increase does not increase the gain above an upper limit. For example, the gain increment might be set so that the gain is increased at a rate of 3 dB per second.

If the condition in step 154 is not met, the process passes to step 158, in which it is determined whether the counted number is greater than or equal to an upper Schmitt trigger threshold. In an illustrative example, the upper Schmitt trigger threshold might be five values out of ten. If so, the process passes to step 160, in which the gain value g, applied by the multiplier 52, is ramped down, provided that this decrease does not reduce the gain below a lower limit.

If the condition in step 158 is not met, i.e. the wind level is between the lower and upper Schmitt trigger thresholds, the process passes to step 162, in which case the gain value g, applied by the multiplier 52, is maintained at its current value.

Thus, while the adjustment of the cut-off frequency of the high pass filter 48 relies only on the incoming smoothed wind-level envelope, the adjustment of the gain uses another degree of controlled smoothing by means of a Schmitt Trigger mechanism, so that this adjustment takes place only if the wind is sustained.

Thus, the Schmitt trigger mechanism determines, during a specified window length, for example of the order of 0.1-0.5 seconds, whether the wind level exceeds a designated wind level, and the gain is altered based on the result. As relatively high wind levels are maintained for a significant time period, the gain value applied by the multiplier 52 is decreased, until, eventually, the ANC is switched off. Once the wind disappears, the ANC gain g is restored to fixed values suitable for the ANC to work normally.

As described here, a Schmitt trigger mechanism is used to control the gain of the ANC system in response to changes in the wind level. This has the effect that the gain is not adjusted in response to rapid changes in the wind level, and so the Schmitt trigger has a low pass effect. This same effect can be achieved by other means. For example, the smoothed wind level values could be applied to an integrator or other low pass filter, with the result of this filtering being used to control the gain of the ANC system.

Figure 8:
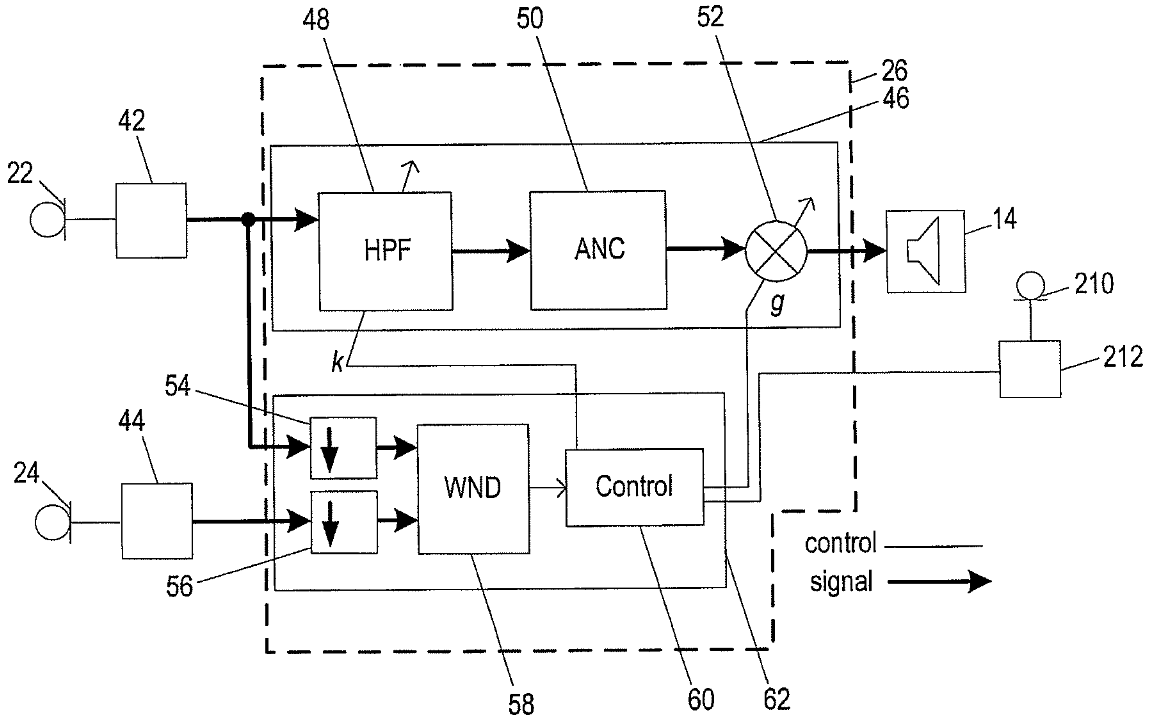
FIG. 8 illustrates an alternative noise reduction system.

FIG. 8 is a block schematic diagram of an alternative noise reduction system. The noise reduction system shown in FIG. 8 is largely the same as that shown in FIG. 3, and only the differences are described herein. Elements of the system shown in FIG. 8 that are the same as those of the system shown in FIG. 3 are indicated by the same reference numerals, and will not be further described.

The noise reduction system of FIG. 8 is an adaptive feed-forward noise cancellation system, in which an error microphone 210 is positioned with respect to the speaker 14, in order to be able to detect sounds output by the speaker that are destined for the entrance of the ear canal of the user. As is conventional, the signal generated by the microphone 210 is passed to an analog-digital converter (ADC) 212, and the magnitude of the signal is used as a measure of the amount of sound leakage past the earphone or handset device towards the user's ear. This is used to determine a desired gain of the noise cancellation system.

Therefore, in this embodiment of the invention, the gain value g is controlled taking account of the signal generated by the microphone 210, with further adjustment based on the detected wind level.

The adjustment of the gain value g can also include an excursion limiter function, for example for loudspeaker protection, to control ramping of the high pass filter 48. That is, when the ambient noise level exceeds a threshold value, the cut-off frequency of the high pass filter 48 can be reduced, to ensure that the signal supplied to the speaker 14 does not exceed a level that would potentially damage the speaker. This function works together with the adaptation of the cut-off frequency of the high pass filter 48 based on the wind noise, as described earlier. If these two functions indicate that the cut-off frequency of the high pass filter 48 should be set to two different frequencies, the control block 60 selects the higher of the two frequencies, so that the system errs on the side of avoiding generating the noise cancellation signal.

There is therefore provided a noise reduction system that can take account of wind noise, and prevent it from adversely affecting noise cancellation.

The invention claimed is:

1. A method of controlling a noise cancellation system, wherein the noise cancellation system comprises:

an input, for receiving a signal representing ambient noise; and a signal processing block, for generating a noise cancellation signal from the signal representing ambient noise, wherein the signal processing block includes a controllable gain value, and a high pass filter with a controllable cut-off frequency, the method comprising:

detecting an amplitude of wind;

controlling the cut-off frequency of the high pass filter based on the detected wind amplitude; and applying a low pass function to the detected wind amplitude, and controlling the controllable gain value based on the output of the low pass function.

2. A method as claimed in claim 1, comprising increasing the cut-off frequency of the high-pass filter when the detected wind amplitude exceeds a first threshold.

3. A method as claimed in claim 2, comprising reducing the cut-off frequency of the high-pass filter when the detected wind amplitude is lower than the first threshold.

4. A method as claimed in claim 1, comprising:

reducing the controllable gain value when the detected wind amplitude exceeds a second threshold level for a time that is greater than a first predetermined fraction of a defined time window; and increasing the controllable gain value when the detected wind amplitude exceeds a second threshold level for a time that is lower than the first predetermined fraction of a defined time window.

5. A method as claimed in claim 1, comprising:

increasing the cut-off frequency of the high-pass filter when the detected wind amplitude exceeds a first threshold;

reducing the controllable gain value when the detected wind amplitude exceeds a second threshold level for a time that is greater than a first predetermined fraction of a defined time window; and increasing the controllable gain value when the detected wind amplitude exceeds a second threshold level for a time that is lower than the first predetermined fraction of a defined time window, wherein the second threshold level is higher than the first threshold level.

6. A method as claimed in claim 1, wherein the step of detecting the amplitude of wind comprises:

obtaining instantaneous wind measurements; and forming a smoothed value as the detected amplitude.

7. A method as claimed in claim 6, wherein the step of forming the smoothed value comprises:

comparing a current instantaneous wind measurement with a previously calculated smoothed value; and if the current instantaneous wind measurement is greater than the previously calculated smoothed value, generating a new smoothed value based on the difference between the current instantaneous wind measurement and the previously calculated smoothed value and an attack coefficient, and if the current instantaneous wind measurement is less than the previously calculated smoothed value, generating a new smoothed value based on the difference between the current instantaneous wind measurement and the previously calculated smoothed value and a decay coefficient.

8. A method as claimed in claim 7, wherein the attack coefficient is greater than the decay coefficient.

9. A method as claimed in claim 8, wherein the attack coefficient is greater than 0.3.

10. A method as claimed in claim 8, wherein the decay coefficient is less than 0.03.

11. A method as claimed in claim 1, comprising obtaining instantaneous wind measurements based on a comparison between a cross correlation between signals obtained from two noise microphones, and a power detected by at least one of said microphones.

12. A noise cancellation system, comprising:

an input, for receiving a signal representing ambient noise;

a signal processing block, for generating a noise cancellation signal from the signal representing ambient noise, wherein the signal processing block includes a controllable gain value, and a high pass filter with a controllable cut-off frequency; and a control block, wherein the control block is adapted to:

detect an amplitude of wind;

control the cut-off frequency of the high pass filter based on the detected wind amplitude; and apply a low pass function to the detected wind amplitude, and control the controllable gain value based on the output of the low pass function.

13. A noise cancellation system as claimed in claim 12, wherein the control block is adapted to increase the cut-off frequency of the high-pass filter when the detected wind amplitude exceeds a first threshold.

14. A noise cancellation system as claimed in claim 13, wherein the control block is adapted to reduce the cut-off frequency of the high-pass filter when the detected wind amplitude is lower than the first threshold.

15. A noise cancellation system as claimed in claim 12, wherein the control block is adapted to:

reduce the controllable gain value when the detected wind amplitude exceeds a second threshold level for a time that is greater than a first predetermined fraction of a defined time window; and increase the controllable gain value when the detected wind amplitude exceeds a second threshold level for a time that is lower than the first predetermined fraction of a defined time window.

16. A noise cancellation system as claimed in claim 15, wherein the control block is adapted to:

increase the cut-off frequency of the high-pass filter when the detected wind amplitude exceeds a first threshold, reduce the controllable gain value when the detected wind amplitude exceeds a second threshold level for a time that is greater than a first predetermined fraction of a defined time window; and increase the controllable gain value when the detected wind amplitude exceeds a second threshold level for a time that is lower than the first predetermined fraction of a defined time window, wherein the second threshold level is higher than the first threshold level.

17. A noise cancellation system as claimed in claim 12, wherein the control block is adapted to detect the amplitude of wind by:

obtaining instantaneous wind measurements; and forming a smoothed value as the detected amplitude.

18. A noise cancellation system as claimed in claim 17, wherein the control block is adapted to form the smoothed value by:

comparing a current instantaneous wind measurement with a previously calculated smoothed value; and if the current instantaneous wind measurement is greater than the previously calculated smoothed value, generating a new smoothed value based on the difference between the current instantaneous wind measurement and the previously calculated smoothed value and an attack coefficient, and if the current instantaneous wind measurement is less than the previously calculated smoothed value, generating a new smoothed value based on the difference between the current instantaneous wind measurement and the previously calculated smoothed value and a decay coefficient.

19. A noise cancellation system as claimed in claim 18, wherein the attack coefficient is greater than the decay coefficient.

20. A noise cancellation system as claimed in claim 19, wherein the attack coefficient is greater than 0.3.

21. A noise cancellation system as claimed in claim 19, wherein the decay coefficient is less than 0.03.

22. A noise cancellation system as claimed in claim 12, wherein the control block is adapted to obtain instantaneous wind measurements based on a comparison between a cross correlation between signals obtained from two noise microphones, and a power detected by at least one of said microphones.

23. A listening device, comprising a noise cancellation system, wherein the noise cancellation system comprises:

an input, for receiving a signal representing ambient noise;

a signal processing block, for generating a noise cancellation signal from the signal representing ambient noise, wherein the signal processing block includes a controllable gain value, and a high pass filter with a controllable cut-off frequency; and a control block, wherein the control block is adapted to:

detect an amplitude of wind;

control the cut-off frequency of the high pass filter based on the detected wind amplitude; and apply a low pass function to the detected wind amplitude, and control the controllable gain value based on the output of the low pass function.

24. A listening device as claimed in claim 23, further comprising at least one earphone.

25. A listening device as claimed in claim 23, comprising a handset.

26. A listening device as claimed in claim 23, comprising a sound reproduction device.

* * * * *